(12) United States Patent
Perrey et al.

(10) Patent No.: US 8,332,050 B2
(45) Date of Patent: Dec. 11, 2012

(54) MEDICAL DEVICE LEAD INCLUDING A UNIFILAR COIL WITH IMPROVED TORQUE TRANSMISSION CAPACITY AND REDUCED MRI HEATING

(75) Inventors: Christopher Perrey, Victoria, MN (US); Bryan A. Clark, Coon Rapids, MN (US); Arthur J. Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 80 days.

(21) Appl. No.: 12/774,170

(22) Filed: May 5, 2010

(65) Prior Publication Data
US 2010/0331936 A1      Dec. 30, 2010

Related U.S. Application Data

(60) Provisional application No. 61/220,658, filed on Jun. 26, 2009.

(51) Int. Cl.
*A61N 1/00* (2006.01)
(52) U.S. Cl. .......................... 607/122; 607/116; 607/119
(58) Field of Classification Search .................. 607/116, 607/119, 122
See application file for complete search history.

(56) References Cited

U.S. PATENT DOCUMENTS

| | | | |
|---|---|---|---|
| 3,614,692 A | 10/1971 | Rozelle et al. | |
| 4,131,759 A | 12/1978 | Felkel | |
| 4,135,518 A | 1/1979 | Dutcher | |
| 4,404,125 A | 9/1983 | Abolins et al. | |
| 4,484,586 A | 11/1984 | McMickle et al. | |
| 4,493,329 A | 1/1985 | Crawford et al. | |
| 4,643,202 A | 2/1987 | Roche | |
| 4,869,970 A | 9/1989 | Gulla et al. | |
| 5,056,516 A | 10/1991 | Spehr | |
| 5,217,010 A | 6/1993 | Tsitlik et al. | |
| 5,222,506 A | 6/1993 | Patrick et al. | |
| 5,231,996 A | 8/1993 | Bardy et al. | |
| 5,243,911 A | 9/1993 | Dow et al. | |
| 5,246,014 A | 9/1993 | Williams et al. | |
| 5,330,522 A | 7/1994 | Kreyenhagen | |
| 5,378,234 A | 1/1995 | Hammerslag et al. | |
| 5,387,199 A | 2/1995 | Siman et al. | |

(Continued)

FOREIGN PATENT DOCUMENTS

CN        1762510 A       4/2006

(Continued)

OTHER PUBLICATIONS

International Search Report and Written Opinion issued in PCT/US2009/032838, mailed May 4, 2009, 14 pages.

(Continued)

*Primary Examiner* — Nicole F. Lavert
(74) *Attorney, Agent, or Firm* — Faegre Baker Daniels LLP

(57) ABSTRACT

A conductor assembly for a medical device lead includes a helically coiled conductor including a plurality of turns having a coil pitch and an outer diameter and consisting of one filar having a filar diameter. The coil pitch and outer diameter are selected based on the filar diameter to minimize heating of the helically coiled conductor in the presence of an MRI field. A polymer sheath is formed about the helically coiled conductor such that the coil pitch of the unifilar helically coiled conductor is maintained. The polymer sheath is configured to increase a torque transmitting capacity of the helically coiled conductor.

23 Claims, 4 Drawing Sheets

U.S. PATENT DOCUMENTS

| | | | |
|---|---|---|---|
| 5,425,755 A | 6/1995 | Doan |
| 5,456,707 A | 10/1995 | Giele |
| 5,483,022 A | 1/1996 | Mar |
| 5,522,872 A | 6/1996 | Hoff |
| 5,522,875 A | 6/1996 | Gates et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,618,208 A | 4/1997 | Crouse et al. |
| 5,728,149 A | 3/1998 | Laske et al. |
| 5,760,341 A | 6/1998 | Laske et al. |
| 5,800,496 A | 9/1998 | Swoyer et al. |
| 5,810,887 A | 9/1998 | Accorti, Jr. et al. |
| 5,833,715 A | 11/1998 | Vachon et al. |
| 5,935,159 A | 8/1999 | Cross, Jr. et al. |
| 5,957,970 A | 9/1999 | Shoberg et al. |
| 5,968,087 A | 10/1999 | Hess et al. |
| 6,057,031 A | 5/2000 | Breme et al. |
| 6,078,840 A | 6/2000 | Stokes |
| 6,106,522 A | 8/2000 | Fleischman et al. |
| 6,143,013 A | 11/2000 | Samson et al. |
| 6,178,355 B1 | 1/2001 | Williams et al. |
| 6,208,881 B1 | 3/2001 | Champeau |
| 6,249,708 B1 | 6/2001 | Nelson et al. |
| 6,256,541 B1 | 7/2001 | Heil et al. |
| 6,289,250 B1 | 9/2001 | Tsuboi et al. |
| 6,295,476 B1 | 9/2001 | Schaenzer |
| 6,400,992 B1 | 6/2002 | Borgersen et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van entem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,721,604 B1 | 4/2004 | Robinson et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,920,361 B2 | 7/2005 | Williams |
| 6,925,334 B1 | 8/2005 | Salys |
| 6,949,929 B2 | 9/2005 | Gray et al. |
| 6,978,185 B2 | 12/2005 | Osypka |
| 6,993,373 B2 | 1/2006 | Vrijheid et al. |
| 6,999,821 B2 | 2/2006 | Jenney et al. |
| 7,013,180 B2 | 3/2006 | Villaseca et al. |
| 7,013,182 B1 | 3/2006 | Krishnan |
| 7,123,013 B2 | 10/2006 | Gray |
| 7,138,582 B2 | 11/2006 | Lessar et al. |
| 7,174,219 B2 | 2/2007 | Wahlstrand et al. |
| 7,174,220 B1 | 2/2007 | Chitre et al. |
| 7,205,768 B2 | 4/2007 | Schulz |
| 7,363,090 B2 | 4/2008 | Halperin et al. |
| 7,388,378 B2 | 6/2008 | Gray et al. |
| 7,389,148 B1 * | 6/2008 | Morgan ........................ 607/116 |
| 7,610,101 B2 | 10/2009 | Wedan et al. |
| 7,765,005 B2 | 7/2010 | Stevenson |
| 7,917,213 B2 | 3/2011 | Bulkes et al. |
| 8,103,360 B2 | 1/2012 | Foster |
| 8,170,688 B2 | 5/2012 | Wedan et al. |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0050680 A1 | 3/2003 | Gibson et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064173 A1 | 4/2004 | Hine et al. |
| 2004/0088033 A1 | 5/2004 | Smits et al. |
| 2004/0122490 A1 | 6/2004 | Reinke et al. |
| 2004/0162600 A1 | 8/2004 | Williams |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0222642 A1 | 10/2005 | Przbyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0283167 A1 | 12/2005 | Gray |
| 2006/0009819 A1 | 1/2006 | Przbyszewski |
| 2006/0030774 A1 | 2/2006 | Gray et al. |
| 2006/0041294 A1 | 2/2006 | Gray |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0106442 A1 | 5/2006 | Richardson et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293737 A1 | 12/2006 | Krishman |
| 2007/0106332 A1 | 5/2007 | Denker et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0058902 A1 | 3/2008 | Gray et al. |
| 2008/0125754 A1 | 5/2008 | Beer et al. |
| 2008/0129435 A1 | 6/2008 | Gray |
| 2008/0132986 A1 | 6/2008 | Gray et al. |
| 2008/0243218 A1 | 10/2008 | Bottomley et al. |
| 2008/0262584 A1 * | 10/2008 | Bottomley et al. ........... 607/119 |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0198314 A1 | 8/2009 | Foster et al. |
| 2009/0281608 A1 | 11/2009 | Foster |
| 2010/0010602 A1 | 1/2010 | Wedan et al. |
| 2010/0234929 A1 | 9/2010 | Scheuermann |
| 2011/0087299 A1 | 4/2011 | Ameri |
| 2011/0093054 A1 | 4/2011 | Ameri et al. |
| 2011/0160828 A1 | 6/2011 | Foster et al. |
| 2011/0238146 A1 | 9/2011 | Wedan et al. |
| 2012/0022356 A1 | 1/2012 | Olsen et al. |
| 2012/0109270 A1 | 5/2012 | Foster |
| 2012/0179233 A1 | 7/2012 | Wedan et al. |

FOREIGN PATENT DOCUMENTS

| | | |
|---|---|---|
| CN | 101039619 A | 9/2007 |
| EP | 0 897 997 B1 | 2/1999 |
| WO | 03/063946 | 8/2003 |
| WO | WO 03/089045 | 10/2003 |
| WO | 2005/030322 | 4/2005 |
| WO | WO2006105066 A2 | 3/2006 |
| WO | 2006/093685 | 9/2006 |
| WO | WO2006093685 A1 | 9/2006 |

| WO | 2006/105066 | 10/2006 |
| WO | WO 2007/047966 | 4/2007 |
| WO | WO 2007/089986 | 8/2007 |
| WO | WO 2007/118194 | 10/2007 |

OTHER PUBLICATIONS

International Search Report and Written Opinion issued in PCT/US2009/038629, mailed Jun. 29, 2009, 11 pages.

International Search Report and Written Opinion issued in PCT/US2008/085518 on Oct. 29, 2009, 15 pages.

Invitation to Pay Additional Fees and Partial Search Report, dated Aug. 17, 2009, issued in PCT/US2008/085533, 6 pages.

Gray, Robert W. et al., "Simple design changes to wires to substantially reduce MRI-induced heating at 1.5 T: implications for implanted leads", Magnetic Resonance Imaging 23 (2005) 887-891.

International Search Report and Written Opinion issued in PCT/US2010/033686 on Aug. 10, 2010, 12 pages.

International Search Report and Written Opinion issued in PCT/US2010/024062, mailed Sep. 27, 2010.

Invitation to Pay Additional Fees and Partial Search Report, issued in PCT/US20101024062, mailed May 7, 2010.

\* cited by examiner

MEDICAL DEVICE LEAD INCLUDING A UNIFILAR COIL WITH IMPROVED TORQUE TRANSMISSION CAPACITY AND REDUCED MRI HEATING

CROSS REFERENCE TO RELATED APPLICATION

This application claims priority to Provisional Application No. 61/220,658, filed Jun. 26, 2009, which is herein incorporated by reference in its entirety.

TECHNICAL FIELD

The present invention relates to implantable medical devices. More particularly, the present invention relates to medical device lead constructions including a unifilar coil with a polymer coating.

BACKGROUND

Implantable medical devices for treating a variety of medical conditions with electrical stimuli are well known. Implantable medical devices generally include a medical electrical lead for delivering an electrical stimulus to a targeted site within a patient's body such as, for example, a patient's heart or nervous system. Such leads generally have an elongated, flexible insulating body, one or more inner conductors extending through lumens formed in the body and one or more exposed electrodes connected to the distal ends of the conductors.

Leads may be introduced into the patient's vasculature at a venous access site and transvenously guided through veins to the sites where the lead electrodes will be implanted or otherwise contact tissue at the targeted therapy site. A pulse generator attached to the proximal ends of the conductors delivers an electrical stimulus therapy to the targeted site via the one or more conductors.

SUMMARY

The present invention relates to a conductor assembly for a medical device lead. The conductor assembly includes a helically coiled conductor including a plurality of turns having a coil pitch and an outer diameter and consisting of one filar having a filar diameter. The coil pitch is one to about two times the filar diameter, and the outer diameter is at least 4.5 times the coil pitch, to minimize heating of the helically coiled conductor in the presence of an MRI field. A polymer sheath is formed about the helically coiled conductor such that the coil pitch of the unifilar helically coiled conductor is maintained. The polymer sheath is configured to increase a torque transmitting capacity of the helically coiled conductor. In one exemplary embodiment, the medical device lead includes an insulated lead body including at least one electrode, and the helically coiled conductor is electrically coupled to the at least one electrode.

In another embodiment of the present invention the helically coiled conductor, the coil pitch, and outer diameter are selected based on the filar diameter to minimize heating of the helically coiled conductor in the presence of an MRI field. A polymer sheath formed about the helically coiled conductor such that the coil pitch of the unifilar helically coiled conductor is maintained. The polymer sheath is partially ablated in a pattern along a length of the polymer sheath that enhances the torque transmitting capacity of the helically coiled conductor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
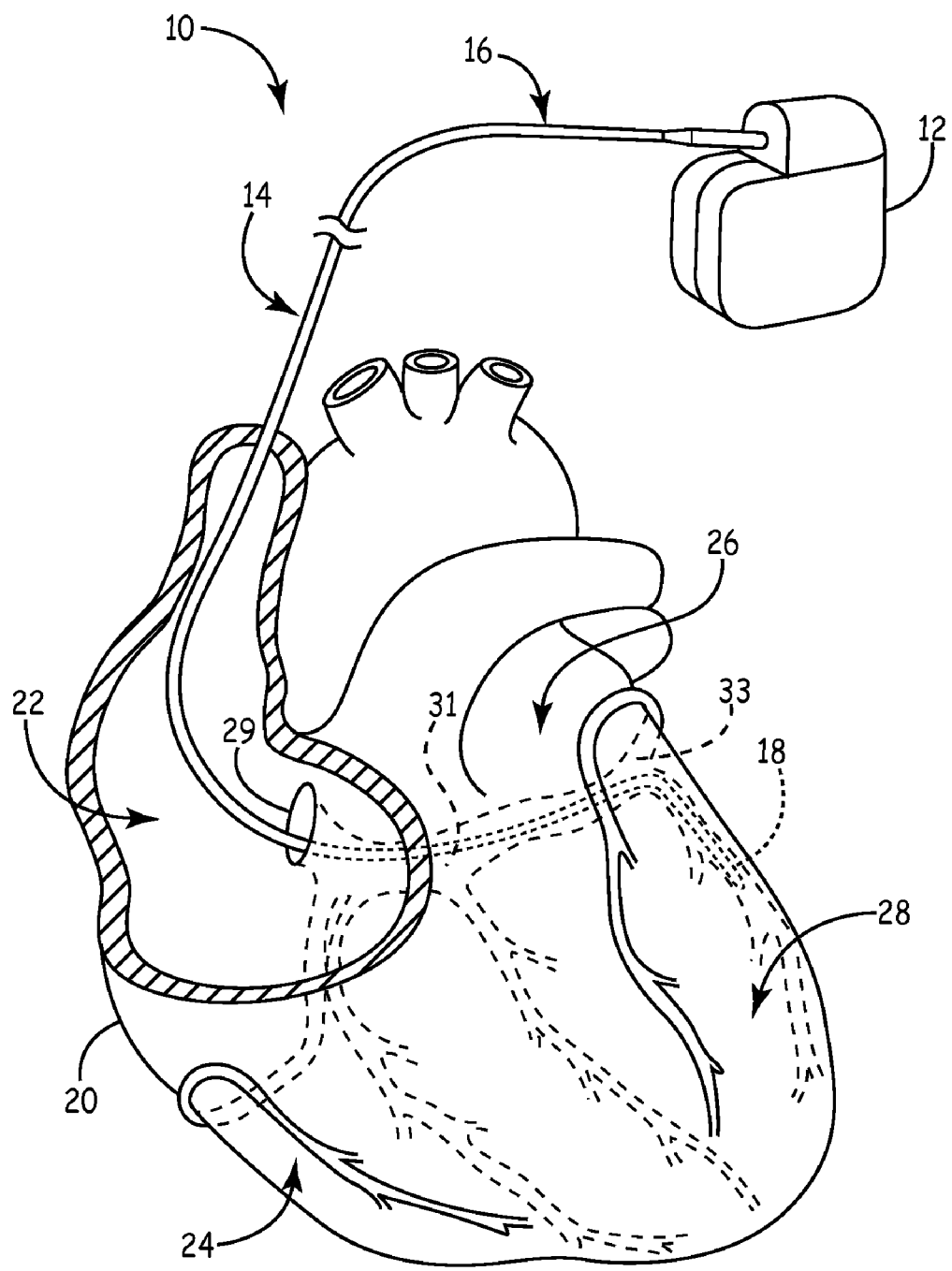
FIG. 1 is a schematic view of a cardiac rhythm management system including a pulse generator coupled to a lead deployed in a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management system 10 including an implantable medical device (IMD) 12 with a lead 14 having a proximal end 16 and a distal end 18. In one embodiment, the IMD 12 includes a pulse generator such as a pacemaker or a defibrillator. The IMD 12 can be implanted subcutaneously within the body, typically at a location such as in the patient's chest or abdomen, although other implantation locations are possible. The proximal end 16 of the lead 14 can be coupled to or formed integrally with the IMD 12. The distal end 18 of the lead 14, in turn, can be implanted at a desired location in or near the heart 20.

As shown in FIG. 1, a distal portion of the lead 14 is disposed in a patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or the great cardiac vein 33. The illustrated position of the lead 14 can be used for sensing or for delivering pacing and/or defibrillation energy to the left side of the heart 20, or to treat arrhythmias or other cardiac disorders requiring therapy delivered to the left side of the heart 20. Additionally, it will be appreciated that the lead 14 can also be used to provide treatment in other regions of the heart 20 (e.g., the right ventricle 24).

Although the illustrative embodiment depicts only a single implanted lead 14, it should be understood that multiple leads can be utilized so as to electrically stimulate other areas of the heart 20. In some embodiments, for example, the distal end of a second lead (not shown) may be implanted in the right atrium 22, and/or the distal end of a third lead (not shown) may be implanted in the right ventricle 24. Other types of leads such as epicardial leads may also be utilized in addition to, or in lieu of, the lead 14 depicted in FIG. 1.

During operation, the lead 14 can be configured to convey electrical signals between the IMD 12 and the heart 20. For example, in those embodiments where the IMD 12 is a pacemaker, the lead 14 can be utilized to deliver electrical stimuli for pacing the heart 20. In those embodiments where the IMD 12 is an implantable cardiac defibrillator, the lead 14 can be utilized to deliver electric shocks to the heart 20 in response to an event such as a heart attack or arrhythmia. In some embodiments, the IMD 12 includes both pacing and defibrillation capabilities.

The electrical signals are carried between the IMD 12 and electrodes at the distal end 18 by one or more conductors extending through the lead 14. The one or more conductors are electrically coupled to a connector suitable for interfacing with the IMD 12 at the proximal end 16 of the lead 14, and to one or more electrodes at the distal end 18. According to the present invention, the one or more conductors are helically coiled including a plurality of turns having a coil pitch and an outer diameter and consisting of one filar having a filar diameter. The coil pitch and outer diameter are selected based on the filar diameter to minimize effects of magnetic resonance imaging (MRI) scans on the functionality and operation of the lead 14. A polymer sheath is formed about the helically coiled conductor such that the coil pitch of the unifilar helically coiled conductor is maintained. The polymer sheath is also configured to increase a torque transmitting capacity of the helically coiled conductor.

Figure 2A:
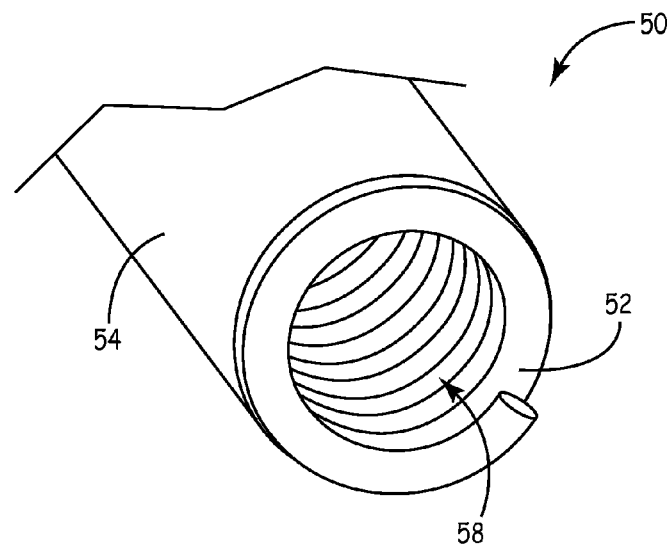
FIG. 2A is a perspective view of a conductor assembly including a unifilar conductive coil and a polymer sheath according to an embodiment of the present invention.
Figure 2B:
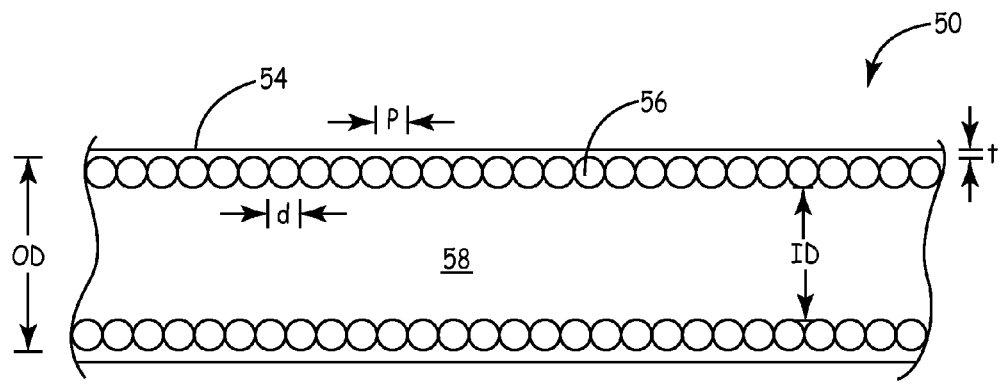
FIG. 2B is a cross-sectional view of the conductor assembly shown in FIG. 2A.

FIG. 2A is a perspective view, and FIG. 2B is a cross-sectional view, of a conductor assembly 50 according to the present invention. The conductor assembly 50 extends through the interior of the lead 14 and includes a coil 52 and a polymer sheath 54. The coil 52 is coupled to the IMD 12 via a connector at the proximal end 16 of the lead 14 and to one or more electrodes at the distal end 18 of the lead 14. While a single coil 52 is shown in FIG. 2A and FIG. 2B, the conductor assembly 50 can be configured to included multiple coils 52 each capable of delivering signals between the IMD 12 and the electrodes at the distal end 18.

The coil 52 includes a single filar 56 that is helically wound around a longitudinal axis of the conductor assembly 50. The filar 56 has a diameter d. A lumen 58 extends through the center of the coil 52 and is suitable for receiving a tool to deliver the lead 14, such as a guidewire or stent. The coil 52 includes a plurality of turns having an outer diameter OD and an inner diameter ID. The coil 52 also has a coil pitch p that extends from the center of a turn of the coil 52 to the center of an adjacent turn of the coil 52.

Exposure of the lead 14 to magnetic resonance imaging (MRI) fields can result in localized heating of the electrodes at the distal end 18 due to excitation of the lead conductors (e.g., coil 52). Conductors with high inductance (>1 µH) are more resistant to excitation in MRI fields. The inductance of the conductor is determined by its geometric properties, including whether the conductor is straight or coiled. For a coiled or wound conductor, such as the coil 52, several parameters influence its inductance, including the coil pitch p, the outer diameter OD, the cross-sectional area of the coil 52, and the number of filars comprising the coil. Thus, the dimensions of the coil 52 may be selected to minimize the effects of magnetic resonance imaging (MRI) fields on the performance and response of the lead 14. For example, for a conductor assembly 50 as shown including a single, unifilar coil 52, a coil pitch p in the range of one to about two times the filar diameter d, and an outer diameter OD at least about 4.5 times the coil pitch p increases the inductance of the coil sufficiently to minimize the energy picked up by the coil 52.

Table 1 below provides example dimensions for the coil 52 to minimize electrode heating caused by MRI fields. The listed dimensions are for a coil 52 having a length (extending from the connector to the distal end 18) in the range of about 450 mm to about 600 mm.

TABLE 1

| Filar Diameter (d) (inch) | Coil Pitch (p) (inch) | Coil Outer Diameter (OD) (inch) |
|---|---|---|
| 0.0005 | 0.0005-0.0008 | 0.002 |
| 0.001 | 0.001-0.002 | 0.004 |
| 0.002 | 0.002-0.003 | 0.009 |
| 0.003 | 0.003-0.004 | 0.013 |
| 0.004 | 0.004-0.005 | 0.020 |
| 0.005 | 0.005-0.007 | 0.022 |
| 0.006 | 0.006-0.008 | 0.027 |
| 0.007 | 0.007-0.009 | 0.031 |
| 0.008 | 0.008-0.010 | 0.036 |
| 0.009 | 0.009-0.011 | 0.040 |
| 0.010 | 0.010-0.012 | 0.045 |
| 0.011 | 0.011-0.013 | 0.049 |

These dimensions are suitable for a conductor assembly 50 including a single, unifilar coil 52. The listed dimensions for the filar diameter d, coil pitch p, and coil outer diameter OD are only by way of example, and other dimensions that reduce electrode heating due to MRI fields to suitable levels are also contemplated. In addition, for embodiments of the conductor assembly 50 including multiple coaxial unifilar coils, these dimensions may change to account for the interaction of the coils with each other in the presence of an MRI field.

The coil 52 with a small diameter OD and having a small pitch p may be prone to damage during construction and use. For example, in active fixation leads, the coil 52 is intended to rotate relative to the lead body and drive torque to extend the fixation helix into tissue of the heart 20. Unifilar coils, such as coil 52, often do not conduct torque well, and the forces typically encountered by the lead 14 can cause the coil 52 to experience stress concentrations in portions of the coil 52, which can lead to premature fatigue of the coil 52. In order to improve the torque transmitting capacity of the coil 52, as well as to maintain the integrity of the coil pitch p, the polymer sheath 54 is formed around the coil 52 such that the polymer sheath 54 covers or envelops the coil 52.

The polymer sheath 54 may be formed over the coil 52 such that portions of the polymer sheath 54 extend between turns of the coil 52 to maintain proper spacing of the coil turns with respect to each other. In some embodiments, the polymer sheath 54 is a sleeve that is pulled over the coil 52 during manufacture. In other embodiments, the polymer sheath 54 is extruded over, molded around, adhered to, or heat shrunk over the coil 52. The polymer sheath 54 may be formed over a coil 52 with an open lumen 58. Alternatively, the coil 52 may be coiled around a tube or cylinder of insulative material, and the polymer sheath 54 subsequently formed around the coil 52.

The polymer sheath 54 is thick enough and is comprised of a material that is stiff enough to increase the torque transmission capacity and maintain the coil pitch p of the coil 52, while still allowing the conductor assembly 50 to sufficiently flex during use. In some embodiments, the thickness t of the polymer sheath 54 is less than about 0.002 inch and is made of a material selected from the group consisting of expanded polytetrafluoroethylene (ePTFE), layered ePTFE, polytetrafluoroethylene (PTFE), ethylene/tetrafluoroethylene copolymer (ETFE), fluorinated ethylene propylene (FEP), silicone, polyurethane, silicone-polyurethane copolymer, and a porous polymer. It will be appreciated that other materials and other thicknesses t are also possible.

The polymer sheath 54 may be adhered to portions of the coil 52 to prevent the polymer sheath 54 from delaminating from the coil 52. Often, this may be accomplished by applying an adhesive material to the coil 52 prior to forming the polymer sheath 54 thereon. However, in some cases, the material used for the polymer sheath 54 does not adhere well to the material used for the coil 52. In order to assure good adhesion, the coil 52 may be coated with a material that bonds well with the polymer sheath 54. For example, the filar 56 may be coated in a suitable polymer prior to coiling the filar 56 into coil 52. Alternatively, the coil 52 may be etched, such as via laser etching, with a pattern that allows for good bonding with the polymer sheath 54.

In some cases, portions of the polymer sheath 54 may be modified to increase the flexibility of the polymer sheath 54. For example, in a J-shaped lead, the lead has a sharp bend at the location of the J-shaped portion. The interaction between certain materials for the polymer sheath 54 and the conductive coil 52 at this sharp bend may cause the conductor assembly 50 to remain in the J-shape, which may prevent manipulation of the J-shaped portion during implantation.

Figure 3A:
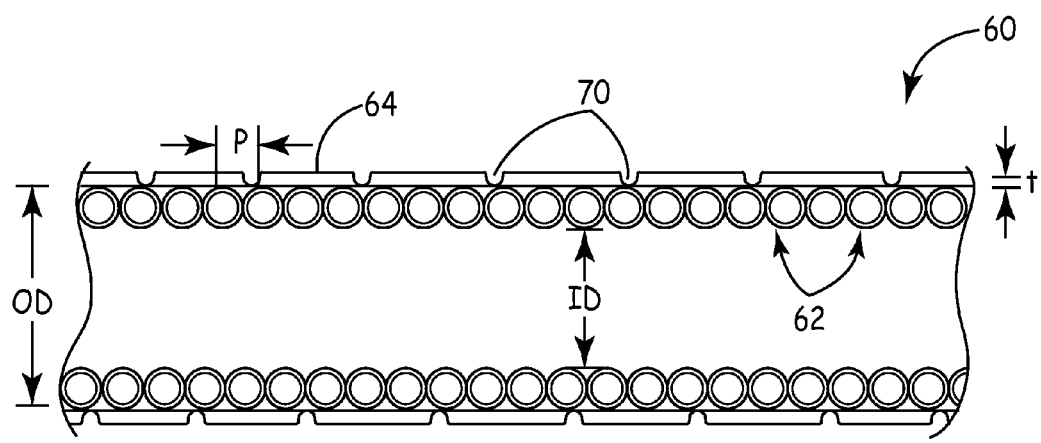
FIG. 3A is a cross-sectional view of a conductor assembly including a partially ablated polymer sheath according to another embodiment of the present invention.
Figure 3B:
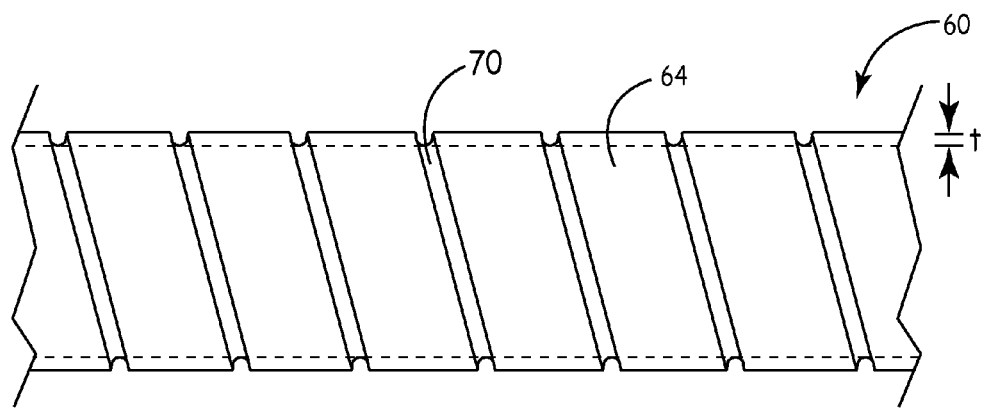
FIG. 3B is a plan view of the conductor assembly shown in FIG. 3A.

FIG. 3A is a cross-sectional view and FIG. 3B is a plan view of a conductor assembly 60 according to another embodiment of the present invention that includes features that improve the flexibility of the conductor assembly 60. The conductor assembly 60 includes a coil 62 and a polymer sheath 64 having material and dimension characteristics substantially similar to the coil 52 and polymer sheath 54, respectively, discussed above with regard to FIGS. 2A and 2B. In this embodiment, the polymer sheath 64 is partially ablated with an ablation pattern 70 along a length of at least a portion of the conductor assembly 60. The polymer sheath 64 is partially ablated in that the polymer sheath 64 is not completely removed (i.e., the coil 52 is not exposed) at the ablated portions of the polymer sheath 64. For example, in a J-shaped lead, the polymer sheath 64 may be partially ablated along the inner radius of the sharp bend at the J-shaped portion. While improving the flexibility of the conductor assembly 60, the remaining thickness of the polymer sheath 64 at the partially ablated locations serve to maintain the pitch p of the coil 62 and improve the torque transmission capacity of the coil 62.

In the embodiment shown, the ablation pattern 70 is a spiral pattern that winds around polymer sheath 64, and about 20% of the polymer sheath 64 is partially ablated. However, it will be appreciated that the ablation pattern 70 may comprise any form, and any percentage of the polymer sheath 64 may be partially ablated, to improve the flexibility of the conductor assembly 60 while maintaining the coil pitch p and improving the torque transmission capacity of the conductor assembly 60.

The polymer sheath 64 may be partially ablated with the ablation pattern 70 using a variety of techniques. In some embodiments, an unmodified polymer sheath 64 is formed over the coil 62 and subsequently modified into the desired pattern. The ablation pattern 70 may be formed by, for example, laser ablating the ablation pattern 70 into the polymer sheath 64. The ablation pattern 70 may alternatively be formed by etching or grinding the ablation pattern 70 into the polymer sheath 64.

Figure 4:
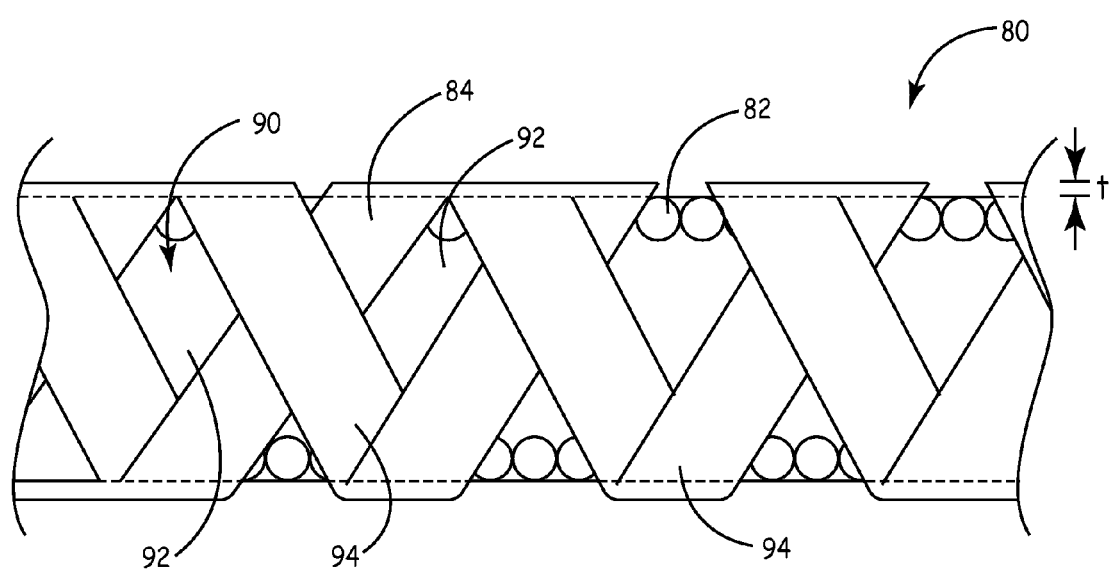
FIG. 4 is a plan view of a conductor assembly including a polymer sheath ablated with a stent like pattern according to another embodiment of the present invention.

FIG. 4 is a plan view of a conductor assembly 80 according to another embodiment of the present invention. The conductor assembly 80 includes a coil 82 and a polymer sheath 84 having material and dimension characteristics substantially similar to the coil 52 and polymer sheath 54, respectively, discussed above with regard to FIGS. 2A and 2B. In this embodiment, the polymer sheath 84 is ablated with a stent-like pattern 90 along a length of at least a portion of the conductor assembly 80. The stent-like pattern 90 includes substantially diamond-shaped ablated portions 92 and unablated portions 94. In some embodiments, the ablated portions 92 are partial ablations that do not extend completely through the thickness t of the polymer sheath 84. In other embodiments, the ablated portions 92 are ablated completely through the thickness t of the polymer sheath 84.

In summary, the present invention relates to a conductor assembly for a medical device lead that includes a helically coiled conductor including a plurality of turns having a coil pitch and an outer diameter and consisting of one filar having a filar diameter. The coil pitch and outer diameter are selected based on the filar diameter to minimize heating of the helically coiled conductor in the presence of an MRI field. In some embodiments, the coil pitch is one to about two times the filar diameter, and the outer diameter is at least 4.5 times the coil pitch. A polymer sheath is formed about the helically coiled conductor such that the coil pitch of the unifilar helically coiled conductor is maintained. The polymer sheath is configured to increase a torque transmitting capacity of the helically coiled conductor. In some embodiments, the polymer sheath is partially ablated in a pattern along a length of the polymer sheath that enhances the torque transmitting capacity of the helically coiled conductor. In one exemplary embodiment, the medical device lead includes an insulated lead body including at least one electrode, and the helically coiled conductor is electrically coupled to the at least one electrode.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead comprising:
at least one electrode;
a helically coiled conductor electrically coupled to the at least one electrode, the helically coiled conductor including a plurality of turns helically wound around a longitudinal axis of the conductor the helically coiled conductor having a coil pitch and an outer diameter, the helically coiled conductor consisting of one filar having a filar diameter, wherein the coil pitch is one to about two times the filar diameter and the outer diameter is at least 4.5 times the coil pitch to minimize heating of the helically coiled conductor in the presence of an MRI field; and
a polymer sheath formed over the helically coiled conductor such that the coil pitch of the unifilar helically coiled conductor is maintained, wherein the polymer sheath is configured to increase a torque transmitting capacity of the helically coiled conductor.

2. The medical device lead of claim 1, wherein the polymer sheath is partially ablated in a pattern along a length of the polymer sheath to increase the flexibility of the conductor assembly around the partial ablation.

3. The medical device lead of claim 1, wherein the helically coiled conductor is adapted to promote adhesion with the polymer sheath.

4. The medical device lead of claim 3, wherein the helically coiled conductor is coated in a material that promotes adhesion between the polymer sheath and the helically coiled conductor.

5. The medical device lead of claim 3, wherein a surface of the helically coiled conductor is etched to promote adhesion with the polymer sheath.

6. The medical device lead of claim 1, wherein the polymer sheath is comprised of a material selected from the group consisting of expanded polytetrafluoroethylene (ePTFE), layered ePTFE, polytetrafluoroethylene (PTFE), ethylene/tetrafluoroethylene copolymer (ETFE), fluorinated ethylene propylene (FEP), silicone, polyurethane, silicone-polyurethane copolymer, and a porous polymer.

7. The medical device lead of claim 1, wherein the filar diameter is less than about 0.005 inch (0.127 mm) and the outer diameter is less than about 0.035 inch (0.889 mm).

8. The medical device lead of claim 1, wherein a thickness of the polymer sheath is less than about 0.002 inch (0.051 mm).

9. A medical device lead comprising:
at least one electrode;
a helically coiled conductor electrically coupled to the at least one electrode, the helically coiled conductor including a plurality of turns helically wound around a longitudinal axis of the conductor the helically coiled conductor having a coil pitch and an outer diameter and consisting of one filar having a filar diameter, wherein the coil pitch and outer diameter are selected based on the filar diameter to minimize heating of the helically coiled conductor in the presence of an MRI field; and
a polymer sheath formed over the helically coiled conductor such that the coil pitch of the unifilar helically coiled conductor is maintained, wherein the polymer sheath is partially ablated in a pattern along a length of the polymer sheath such that a thickness of the polymer sheath along the partially ablated pattern is less than a thickness of non-ablated portions of the polymer sheath.

10. The medical device lead of claim 9, wherein the coil pitch is one to about two times the filar diameter.

11. The medical device lead of claim 9, wherein the outer diameter is at least 4.5 times the coil pitch.

12. The medical device lead of claim 9, wherein the helically coiled conductor is adapted to promote adhesion with the polymer sheath.

13. The medical device lead of claim 12, wherein the helically coiled conductor is coated in a material that promotes adhesion between the polymer sheath and the helically coiled conductor.

14. The medical device lead of claim 12, wherein a surface of the helically coiled conductor is etched to promote adhesion with the polymer sheath.

15. The medical device lead of claim 9, wherein the polymer sheath is comprised of a material selected from the group consisting of expanded polytetrafluoroethylene (ePTFE), layered ePTFE, polytetrafluoroethylene (PTFE), ethylene/tetrafluoroethylene copolymer (ETFE), fluorinated ethylene propylene (FEP), silicone, polyurethane, silicone-polyurethane copolymer, and a porous polymer.

16. The medical device lead of claim 9, wherein the filar diameter is less than about 0.005 inch (0.127 mm) and the outer diameter is less than about 0.035 inch (0.889 mm).

17. A conductor assembly for a medical device lead, the conductor assembly comprising:
a helically coiled conductor configured to be coupled to a pulse generator at a proximal end and at least one electrode at a distal end, the helically coiled conductor including a plurality of turns helically wound around a longitudinal axis of the conductor assembly, the helically coiled conductor having a coil pitch and an outer diameter, the helically coiled conductor consisting of one filar having a filar diameter, wherein the coil pitch is one to about two times the filar diameter and the outer diameter is at least 4.5 times the coil pitch to minimize heating of the helically coiled conductor in the presence of an MRI field; and
a polymer sheath formed over the helically coiled conductor such that the coil pitch of the unifilar helically coiled conductor is maintained, wherein the polymer sheath is configured to increase a torque transmitting capacity of the helically coiled conductor.

18. The conductor assembly of claim 17, wherein the polymer sheath is partially ablated in a pattern along a length of the polymer sheath to increase the flexibility of the conductor assembly around the partial ablation.

19. The conductor assembly of claim 17, wherein the helically coiled conductor is adapted to promote adhesion with the polymer sheath.

20. The conductor assembly of claim 19, wherein the helically coiled conductor is coated in a material that promotes adhesion between the polymer sheath and the helically coiled conductor.

21. The conductor assembly of claim 19, wherein a surface of the helically coiled conductor is etched to promote adhesion with the polymer sheath.

22. The conductor assembly of claim 17, wherein the polymer sheath is comprised of a material selected from the group consisting of expanded polytetrafluoroethylene (ePTFE), layered ePTFE, polytetrafluoroethylene (PTFE), ethylene/tetrafluoroethylene copolymer (ETFE), fluorinated ethylene propylene (FEP), silicone, polyurethane, silicone-polyurethane copolymer, and a porous polymer.

23. The conductor assembly of claim 17, wherein the filar diameter is less than about 0.005 inch (0.127 mm) and the outer diameter is less than about 0.035 inch (0.889 mm).

* * * * *